(12) United States Patent
Sato et al.

(10) Patent No.: US 7,834,061 B2
(45) Date of Patent: Nov. 16, 2010

(54) PROCESS FOR PRODUCING 1,4-DIHYDROXY-2-NAPHTHOIC ACID

(75) Inventors: Yoshio Sato, Kanagawa (JP); Seiya Makino, Kanagawa (JP); Nobuo Yoda, Tokyo (JP); Kakuhei Isawa, Tokyo (JP); Tomonori Kamiyama, Kanagawa (JP); Kenichi Hojo, Kanagawa (JP); Mizue Saito, Kanagawa (JP); Naoki Taketomo, Tokyo (JP); Keisuke Furuichi, Tokyo (JP); Shuji Ikegami, Kanagawa (JP)

(73) Assignee: Meiji Dairies Corporation, Tokyo (JP)

( * ) Notice: Subject to any disclaimer, the term of this patent is extended or adjusted under 35 U.S.C. 154(b) by 0 days.

(21) Appl. No.: 12/543,814

(22) Filed: Aug. 19, 2009

(65) Prior Publication Data

US 2009/0312425 A1 Dec. 17, 2009

Related U.S. Application Data

(62) Division of application No. 12/100,075, filed on Apr. 9, 2008, now Pat. No. 7,629,155, which is a division of application No. 10/486,421, filed as application No. PCT/JP02/08010 on Aug. 6, 2002, now Pat. No. 7,374,915.

(30) Foreign Application Priority Data

Aug. 10, 2001 (JP) ............... 2001-244475

(51) Int. Cl.
*A61K 31/19* (2006.01)
*C12P 7/40* (2006.01)
*C07C 63/34* (2006.01)
(52) U.S. Cl. .................. 514/569; 435/136; 562/467
(58) Field of Classification Search .......... 435/136; 562/467; 514/569
See application file for complete search history.

(56) References Cited

FOREIGN PATENT DOCUMENTS

| JP | 57-128655 | | 8/1982 |
|----|-----------|---|--------|
| JP | 59-186942 | | 10/1984 |
| JP | 60-104037 | | 6/1985 |
| JP | 8-98677 | | 4/1996 |
| JP | 08098677 | * | 4/1996 |
| JP | 9-75095 | | 3/1997 |
| JP | 10-14589 | | 1/1998 |
| JP | 11-228424 | | 8/1999 |
| JP | 2000-86525 | | 3/2000 |
| JP | 2000-256201 | | 9/2000 |
| JP | 2001-169749 | | 6/2001 |
| WO | 01/28547 | | 4/2001 |

OTHER PUBLICATIONS

Kenichi Hojo, et al., "Bifidogenic Grown Stimulator Produced by Propionic Acid Bacteria", Milk Science, vol. 49, No. 3, XP-008051230, 2000, pp. 161-167.

(Continued)

*Primary Examiner*—Taylor Victor Oh
(74) *Attorney, Agent, or Firm*—Oblon, Spivak, McClelland, Maier & Neustadt, L.L.P.

(57) ABSTRACT

A composition containing 1,4-dihydroxy-2-naphthoic acid at a high concentration is obtained by intracellularly and extracellularly producing 1,4-dihydroxy-2-naphthoic acid using a bacterium belonging to the genus *Propionibacterium* and collecting it. This composition is efficacious in improving intestinal flora, alleviating abdominal ailments in association with the intake of milk, and preventing metabolic bone diseases.

14 Claims, 4 Drawing Sheets

*: Wilcoxon test

OTHER PUBLICATIONS

Hiroharu Mori, et al., "Isolation and Structural Identification of Bifidogenic Growth Stimulator Produced by Propionibacterium freudenreichii", Journal of Dairy Science, vol. 80, No. 9, XP-009002165, 1997, pp. 1959-1964.

Tsutomu Kaneko, et al., "Growth Stimulator for Bifidobacteria Produced by Propionibacterium Freudenreichii and Several Intestinal Bacteria", Journal of Dairy Science, vol. 77, No. 2, XP-000590802, Feb. 1994, pp. 393-404.

Isawa Kakuhei, et al., "Isolation and Identification of a New Bifidogenic Growth Stimulator Produced by Propionibacterium Freudenreichii ET-3", Biosci. Biotechnol. Biochem., vol. 66, No. 3, XP-008041283, Mar. 2002, pp. 679-681.

Meganathan, R., et al., "Menaquinone (Vitamin $K_2$) biosynthesis: Conversion of o-succinylbenzoic acid to 1,4-dihydroxy-2-napthoic acid by Mycobacterium phylei enzymes", J. Bacteriol., Oct. 1979, vol. 140, No. 1, pp. 92-98, full text.

Kaneko, T., and Noda, K., "Bifidogenic growth stimulator produced by propionic acid bacteria", Japanese Journal of Dairy and Food Science, 1995, vol. 45, No. 4, pp. 83-91, table 2 to 4.

Norihiro Azuma, et al., Agric. Biol. Chem., vol. 48, No. 8, pp. 2159-2162, 1984.

Shoji Usami, et al., Nippon Nogeikagaku Kaishi, vol. 55, No. 6, pp. 499-501, 1981.

Paul György, et al., Proc. Soc. Exp. Biol. Med., vol. 90, pp. 219-223.

Anatoly Bezkorovainy, et al., The American Journal of Clinical Nutrition, vol. 32, pp. 1428-1483, 1979.

Zenzo Tamura, et al., Chem. Pharm. Bull, vol. 14, No. 10, p. 1191, Jun. 7, 1966.

Proceedings of Tohoku Fukushi University, vol. 10, pp. 313-331, 1986.

Heide et al, Enzymatic Synthesis, Characterization, and Metabolism of the Coenzyme A ester of o-succinylbenzoic acid, an intermediate in Menaquinone Biosynthesis, The Journal of Biological Chemistry, vol. 257, No. 13, July Issue 10, p. 7396-7400, 1982.

Berge et al., Journal of Pharmaceutical Sciences, vol. 66, No. 1, 1977, p. 1-18.

* cited by examiner

*: Wilcoxon test

*: Wilcoxon test

US 7,834,061 B2

PROCESS FOR PRODUCING 1,4-DIHYDROXY-2-NAPHTHOIC ACID

CROSS-REFERENCE TO RELATED APPLICATIONS

The present application is a divisional of U.S. patent application Ser. No. 12/100,075, filed on Apr. 9, 2008, which is a divisional of U.S. patent application Ser. No. 10/486,421, filed on Feb. 10, 2004, which is a 35 U.S.C. §371 National Stage patent application of International patent application PCT/JP02/08010, filed on Aug. 6, 2002, which claims priority to Japanese patent application JP 2001-244475, filed on Aug. 10, 2001.

TECHNICAL FIELD

The present invention relates to an industrial production process for 1,4-dihydroxy-2-naphthoic acid (or 1,4-dihydroxy-2-naphthalene carboxylic acid) (hereinafter may be referred to simply as "DHNA"); to a drug containing the compound; and to food and beverage which contain the compound and thus are useful for improving intestinal flora, alleviating abdominal ailments caused by lactose intolerance, and for preventing or treating metabolic bone diseases.

BACKGROUND ART

Comparative studies on the intestinal flora found in breast-fed infants and that in bottle-fed infants have suggested that *bifidobacteria* are useful for improving human health. As has been confirmed, the amount of *bifidobacteria* in the body is significantly reduced by gastrointestinal tract diseases or similar diseases, or aging, and promotion of proliferation of intestinal *bifidobacteria* is effective for preventing carcinogenesis, intestinal putrefaction, infectious diseases, and other health problems. Therefore, selective proliferation of intestinal *bifidobacteria* is considered very important for maintaining health and preventing and treating various diseases, including life-style-related diseases.

Conventionally, several substances capable of promoting proliferation of useful *bifidobacteria*—such a substance is called a "Bifidus factor"—have been studied and reported. Examples of the substances include N-acetylglucosamine, which is found in breast milk (Proc. Soc. Exp. Biol. Med., 90, 219 (1955)); peptide-related substances (Am. J. Clin. Nutr., 32, 1428 (1974) and Agric. Biol. Chem., 48, 2159 (1984)); carrot extracts (Journal of Japan Society for Bioscience, Biotechnology, and Agrochemistry, 55, 499 (1981) and Chem. Pharm. Bull., (Tokyo) 14, 1191 (1966)); and sugar-related substances (Proceedings of Tohoku Fukushi University, 10, 313 (1986)).

However, preparation of any of these substances capable of promoting proliferation of *bifidobacteria* requires an intricate process, and the effect of such substances in terms of selective proliferation of merely *bifidobacteria* needs to be improved.

In view of the foregoing, the present inventors have performed extensive studies on compounds capable of selectively promoting proliferation of *bifidobacteria*, and as a result have found that certain types of naphthoquinone derivatives and naphthalene derivatives exhibit strong activity in promoting proliferation of various *bifidobacteria* (e.g., *Bifidobacterium longum, B. breve, B. adolescentis, B. bifidum, B. infantis, B. animalis*, and *B. pseudolongum*). Also, the present inventors have disclosed, in addition to these known compounds, a highly active *bifidobacteria* proliferation promotion substance, and have confirmed that this substance is 2-amino-3-carboxy-1,4-naphthoquinone, which is a conventionally unknown (in other words, novel) substance, and is produced intracellularly and extracellularly by a bacterium belonging to the genus *Propionibacterium* (Japanese Patent Application Laid-Open (kokai) No. 8-98677). Furthermore, the present inventors have found that 2-amino-3-carboxy-1,4-naphthoquinone is useful as a drug for preventing or treating metabolic bone diseases such as osteoporosis (WO 01/28547).

Meanwhile, DHNA has been known to be useful as an industrial material such as a dye, a pigment, or a photosensitive material, and various organic chemical synthetic methods for DHNA have been developed (e.g., Japanese Patent Application Laid-Open (kokai) Nos. 57-128655, 59-186942, and 60-104037). However, such a conventional synthetic method requires high-temperature, high-pressure reaction in an organic solvent, or employment of, for example, an inedible reagent as a catalyst or the like. In addition, difficulty is encountered in completely removing, from DHNA produced through such a method, solvents or reagents employed for production thereof. Therefore, DHNA produced through such a conventional production method has not been considered to be useful in foods and beverages or in drugs.

DISCLOSURE OF THE INVENTION

The present inventors have conducted further studies on various compounds exhibiting a proliferation promotion effect specific to *bifidobacteria*, and as a result have found that a large amount of 1,4-dihydroxy-2-naphthoic acid (DHNA) is produced intracellularly and extracellularly by a bacterium belonging to the genus *Propionibacterium*, and that a composition containing 1,4-dihydroxy-2-naphthoic acid collected from the resultant culture broth, or 1,4-dihydroxy-2-naphthoic acid or a salt thereof, exhibits the effect of alleviating abdominal ailments caused by milk intolerance, which occur upon ingestion of milk, and is useful for preventing or treating metabolic bone diseases, since this compound promotes differentiation of osteoblasts and expression of osteoblast function, and suppresses formation of osteoclasts. The present invention has been accomplished on the basis of these findings. Examples of 1,4-dihydroxy-2-naphthoic acid salts include pharmacologically or sitologically acceptable salts. Typical examples of the salts include acetates, benzenesulfonates, benzoates, bicarbonates, lactates, and citrates, which should not be construed as limiting the present invention thereto.

Accordingly, the present invention provides a process for producing 1,4-dihydroxy-2-naphthoic acid, which comprises culturing a microorganism capable of producing 1,4-dihydroxy-2-naphthoic acid, to thereby allow the microorganism to produce 1,4-dihydroxy-2-naphthoic acid in culture broth, and collecting the thus-produced 1,4-dihydroxy-2-naphthoic acid.

The present invention also provides a composition containing 1,4-dihydroxy-2-naphthoic acid, which composition is produced through the aforementioned production process.

The present invention also provides food and beverage for alleviating abdominal ailments, an agent for alleviating abdominal ailments, an intestinal function regulating agent, food and beverage for preventing or treating metabolic bone diseases, or an agent for preventing or treating metabolic bone diseases, which comprises, as an active ingredient, a composition containing 1,4-dihydroxy-2-naphthoic acid, which composition is produced through the aforementioned production process, or 1,4-dihydroxy-2-naphthoic acid or a salt thereof.

The present invention also provides use of a composition containing 1,4-dihydroxy-2-naphthoic acid, which composition is produced through the aforementioned production process, or 1,4-dihydroxy-2-naphthoic acid or a salt thereof, for producing food and beverage for alleviating abdominal ailments, an agent for alleviating abdominal ailments, an intestinal function regulating agent, food and beverage for preventing or treating metabolic bone diseases, or an agent for preventing or treating metabolic bone diseases.

The present invention also provides a method for treating abdominal ailments, a method for regulating intestinal function, or a method for treating metabolic bone diseases, which comprises administering, to a subject in need thereof, an effective dose of a composition containing 1,4-dihydroxy-2-naphthoic acid, which composition is produced through the aforementioned production process, or 1,4-dihydroxy-2-naphthoic acid or a salt thereof.

BEST MODES FOR CARRYING OUT THE INVENTION

Figure 1:
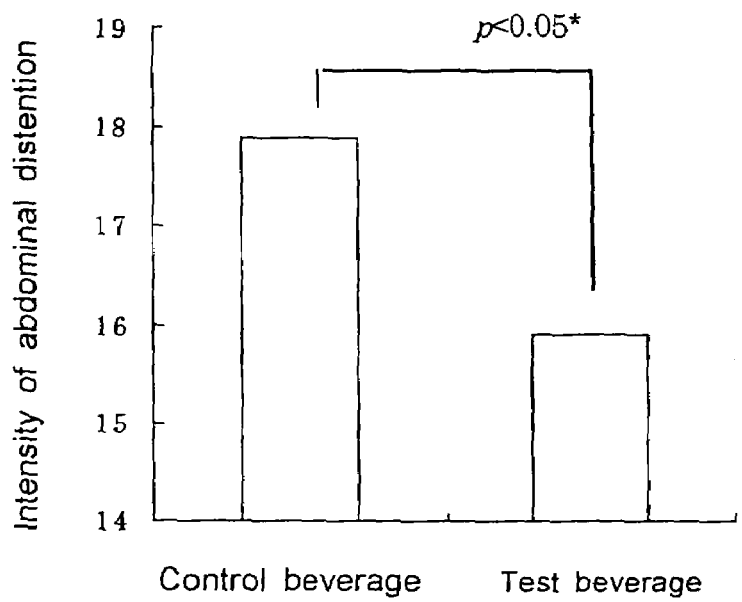
FIG. 1 is a graph showing the intensity of abdominal distention reported by subjects until six hours has elapsed after ingestion of a milk beverage incorporating the composition of the present invention containing a high concentration of DHNA.

The present invention employs a bacterium capable of producing 1,4-dihydroxy-2-naphthoic acid (DHNA). Examples of the genus to which such a bacterium belongs include *Propionibacterium, Enterobacter, Sporolactobacillus*, and *Bacillus*. Most of these microorganisms have conventionally been employed for producing foods and beverages and drugs, and therefore, employment of such a bacterium for producing a DHNA-containing food and beverage or a DHNA-containing drug is preferred. Examples of propionic acid bacteria include bacteria for producing cheese, such as *Propionibacterium freudenreichii, P. thoenii, P. acidipropionici*, and *P. jensenii; P. avidum; P. acnes; P. lymphophilum*; and *P. granulosam*. Examples of bacteria belonging to the genus *Bacillus* include *Bacillus subtilis* and *Bacillus coagulans*. The microorganism employed in the present invention is preferably *Propionibacterium freudenreichii*. Specific examples include *P. freudenreichii* IFO 12424 and *P. freudenreichii* ATCC 6207.

In order to produce DHNA through the process of the present invention, firstly, a strain capable of producing DHNA is aerobically or anaerobically cultured in a nutrient-containing medium in which general microorganisms can be grown. The nutrient may be a known nutrient which has conventionally been employed for culturing of microorganisms. The nutrient-containing medium is particularly preferably a medium containing skim milk powder; a medium containing trypticase, phytone, yeast extract, and glucose; or a medium predominantly containing lactase-treated whey mineral, and whey powder, protease-treated whey powder, a whey protein concentrate, or a product obtained through treatment of the concentrate. In the present invention, most preferably, protease-treated skim milk powder is employed as a protein source in a medium. In the case where protease-treated skim milk powder is employed in a medium, when at least one of yeast extract and lactose is employed as an additive during the course of culturing, the amount of DHNA produced in the resultant culture broth can be increased. During the course of culturing, in place of lactose, glucose or lactase-treated lactose may be employed as an additive. However, when protease-treated skim milk powder is employed as a primary raw material for a medium, most preferably, lactose is employed as a sugar in the medium. Next will be described an exemplary medium preparation method in the case where protease-treated skim milk powder is employed as a medium raw material.

Skim milk powder is dissolved in water such that the skim milk powder concentration is 10% (w/v), followed by protein degradation by means of protease. The amount of protease to be employed is 0.25% (w/w) on the basis of the entirety of the skim milk powder. Protein degradation is performed at 47° C. and a pH of 6.8 for six hours, and an aqueous potassium carbonate solution is employed for pH adjustment during protein degradation. The skim milk powder concentration (final medium concentration) is regulated to 10% (w/v), and finally, yeast extract is added such that the amount of the yeast extract is 1 to 10% (w/w), preferably 3 to 7% (w/w), on the basis of the entirety of the skim milk powder.

A DHNA-producing strain may be cultured by means of any of a variety of known aerobic and anaerobic culture methods, but an aerobic or anaerobic culture method employing a liquid medium is most preferred, from the viewpoint of mass production of DHNA. Culturing is performed under the following conditions: incubation temperature: about 20 to about 40° C., medium pH: neutral to slightly acidic (preferably 5.5 to 7.5). In the case of liquid culturing, when about one to about five days elapse after initiation of culturing, DHNA is accumulated in the medium and the strain. The amount of DHNA to be produced increases through addition of lactose during the course of culturing. The thus-produced DHNA may be collected from the resultant culture broth immediately after completion of culturing. However, preferably, the culture broth is cooled (at 3 to 20° C., more preferably at about 10° C.) and stored (preferably for about two to about four weeks), to thereby allow DHNA to further accumulate in the culture broth.

A DHNA collection method will next be described. Preferably, the above-obtained culture broth is subjected to adsorption chromatography. Examples of the adsorbent which may be employed include absorbents for reversed-phase chromatography, such as activated carbon and synthetic absorbents (e.g., Diaion HP-20, product of Mitsubishi Chemical Corporation). Firstly, a column is filled with an absorbent, and the column is washed with a 0.5% (w/v) aqueous sodium ascorbate solution. Subsequently, the above-obtained culture broth is added to the column (a fluid which passes through the column is denoted by "pass"), and a water-soluble fraction is removed from the culture broth by use of a 0.5% (w/v) aqueous sodium ascorbate solution. Thereafter, the resultant culture broth is subjected to elution with ethanol containing 0.5% (w/v) sodium ascorbate, and the ethanol-eluted fraction is concentrated, to thereby produce a composition containing a high concentration of DHNA. When the DHNA-containing composition is further purified, pure DHNA or a salt thereof can be produced. In place of ethanol, methanol may be employed for eluting DHNA from the column.

Examples of DHNA salts include pharmacologically or sitologically acceptable salts. Typical examples of the salts include acetates, benzenesulfonates, benzoates, bicarbonates, lactates, and citrates, which should not be construed as limiting the present invention thereto.

DHNA is contained in the culture broth of the DHNA-producing bacterium (intracellularly and/or extracellularly). Therefore, rather than being subjected to adsorption chromatography, the culture broth per se may be concentrated by use of, for example, a rotary evaporator, to thereby yield a composition containing a high concentration of DHNA. Preferably, the bacterium cells are separated from the culture broth by means of a generally employed centrifugation technique, and the resultant supernatant is concentrated. The physical form of the thus-obtained composition varies in accordance with the intended use thereof; for example, the composition may be used in liquid form or may be formed into a powdery product.

The term "milk intolerance" refers to the case where abdominal ailments such as abdominal pain, borborygmus, and diarrhea occur after ingestion of milk. Most of such abdominal ailments are associated with lactose intolerance, which occurs as a result of ingestion of lactose contained in milk, etc. In many cases, lactose intolerance is caused by deficiency or reduction of lactase activity in the small intestine. The composition of the present invention, or DHNA or a salt thereof (hereinafter may be referred to simply as "the composition, etc.") exhibits the effect of alleviating abdominal ailments which occur upon ingestion of milk. In addition, the composition, etc. exhibits the effect of promoting differentiation of osteoblasts and expression of osteoblast function, as well as the effect of suppressing formation of osteoclasts, and therefore is useful for preventing or treating metabolic bone diseases such as osteoporosis. The composition, etc. may assume the form of food and beverage, or a drug. For example, through direct administration of the composition, etc. in the form of a drug, through direct ingestion of the composition, etc. in the form of a food for special use (e.g., a food for specific health use) or a nutritional food, or through ingestion of various foods (e.g., milk, fermented milk, and yogurt) containing the composition, etc., intestinal flora can be improved, abdominal ailments which occur, for example, upon ingestion of milk can be alleviated, and metabolic bone diseases can be prevented or treated.

In the case where the composition of the present invention, or DHNA or a salt thereof is employed as a drug, the physical form of the composition, etc. can be appropriately chosen in accordance with the manner of administration. Examples of the physical form include oral forms such as a tablet, a capsule, a granule, a powder, and a syrup. Such a drug product can be prepared by means of a customary method making use, as a primary agent, of a known auxiliary agent which is generally employed in the drug preparation technical field, such as an excipient, a binder, a disintegrating agent, a lubricant, a flavoring agent, a deodorant, a dissolution promoter, a suspending agent, or a coating agent.

When applied to a human, preferably, such a drug product is orally administered thereto. The effective dose of DHNA (i.e., an active ingredient) which is orally administered to a patient to be treated varies in accordance with the age and pathological conditions of the patient, but in general, the daily dose of DHNA per kg body weight of a human is 0.03 to 3 µg, preferably 0.1 to 1 µg.

When orally administered, the composition of the present invention, or DHNA or a salt thereof attains its intended purposes; i.e., improvement of intestinal flora, alleviation of abdominal ailments which occur upon ingestion of milk, and prevention or treatment of metabolic bone diseases. Therefore, the composition, etc. can be employed in the form of food and beverage. Such DHNA-containing food and beverage can be prepared by means of any of various techniques; for example, the composition of the present invention containing a high concentration of DHNA, or DHNA or a salt thereof is added to any of a variety of auxiliary agents or foods and beverages, to thereby prepare various foods and beverages (e.g., drink products and tablets); or the composition, etc. is added directly to foods and beverages. The thus-prepared food and beverage enables DHNA to be ingested over a long period of time, and thus can be commercially provided in the form of general food and beverage, food for special use (e.g., food for specific health use), or nutritional food.

EXAMPLES

The present invention will next be described in more detail with reference to Test Example and Examples, but the present invention is not limited to these Examples.

Test Example 1

Screening of DHNA-Producing Bacteria Culturing Conditions

Each of the below-described test bacteria was inoculated into a medium containing skim milk powder (described below in Example 1), and the bacterium was anaerobically cultured by means of the GasPak method at 37° C. for 18 to 72 hours.

(A) *Propionibacterium freudenreichii* IFO 12424 (culture time: 72 hours)
(B) *Propionibacterium acidipropionicii* IFO 12425 (72 hours)
(C) *Propionibacterium jensenii* IFO 12427 (72 hours)
(D) *Lactococcus lactis* ATCC 10697 (24 hours)
(E) *Leuconostoc mesenteroides* JCM 9700 (24 hours)
(F) *Lactobacillus acidophilus* ATCC 4357 (18 hours)
(G) *Lactobacillus plantarum* IFO 12006 (18 hours)
(H) *Lactobacillus rhamnosus* JCM 1136 (18 hours)
(I) *Lactobacillus casei* ATCC 7469 (18 hours)
(J) *Bifidobacterium longum* ATCC 15707 (18 hours)
(K) *Bifidobacterium bifidum* ATCC 11146 (18 hours)
(L) *Bifidobacterium adolescentis* ATCC 15703 (18 hours)
(M) *Bifidobacterium breve* ATCC 15700 (18 hours)

DHNA Analysis Conditions (HPLC Analysis)
Column: C18, filler particle size: 3 µm, inner diameter: 4.6 mm, length: 150 mm (C18: Cadenza CD-C18, product of Imtakt Corporation)
Eluent:acetonitrile:methanol:water:acetic acid=10:20:200:0.1 (pH: 7.0 (adjusted with 5% aqueous ammonia))
Flow rate: 1.5 mL/min
Injection amount: 20 µl
Detector: UV 254 nm HPLC Sample Preparation Method
Sodium ascorbate (0.1% (w/v)) was added to the above-obtained culture broth (10 ml), the pH of the resultant mixture was adjusted to 7.0, and water was added to the mixture such that the total volume of the resultant mixture was 20 ml. Thereafter, an aliquot (3 ml) of the mixture was mixed with methanol (3 ml), and the resultant mixture was subjected to centrifugation at 3,000 rpm for 10 minutes. The thus-obtained supernatant was subjected to filtration by use of a 0.45-µm filter.

Quantification of DHNA

The amount of DHNA contained in the above-prepared HPLC sample was calculated on the basis of the following previously obtained data of a commercially available DHNA standard (product of Wako Pure Chemical Industries, Ltd.): retention time=around 13 minutes, and relationship between HPLC peak area and DHNA concentration (calibration curve).

As a result, each of the culture broths of *Propionibacteria* (A) through (C) was found to contain DHNA in an amount of 3.0 µg/ml or more. Although a trace amount of DHNA was detected in the culture broth of *Lactococcus* (D) or *Leuconostoc* (E), no DHNA was detected in each of the culture broths of *Lactobacilli* (F) through (I) and *Bifidobacteria* (J) through (M). That is, *Propionibacterium* was found to be desirable as a DHNA-producing bacterium employed in the present invention (Table 1). Meanwhile, *Bacillus subtilis* was aerobically cultured by use of a medium similar to that described above. As a result, the thus-obtained culture broth was found to contain DHNA.

TABLE 1

| Test Bacteria | Culture time (hr) | DHNA (µg/ml) |
|---|---|---|
| (A) | 72 | 3.0 |
| (B) |  | 3.2 |
| (C) |  | 3.6 |
| (D) | 24 | 0.1 |
| (E) | 24 | 0.2 |
| (F) | 18 | N.D. |
| (G) |  | N.D. |
| (H) |  | N.D. |
| (I) |  | N.D. |
| (J) | 18 | N.D. |
| (K) |  | N.D. |
| (L) |  | N.D. |
| (M) |  | N.D. |

N.D.: not detected

Example 1

Production Process for DHNA-Containing Composition

Beer yeast extract (product of Asahi Breweries, Ltd.) (0.1% (w/v)) was added to a skim milk medium (a solution containing 10 wt. % skim milk powder) which had been prepared by dissolving skim milk powder in water such that the skim milk powder concentration was 10% (w/v). The resultant medium (50 L) was placed into 20 Erlenmeyer flasks (volume: 5 L each) in a divided manner, and the medium in each of the flasks was sterilized at 121° C. for seven minutes by use of an autoclave. An activated culture broth of *Propionibacterium freudenreichii* IFO 12424 strain (60 ml) was inoculated into each of the resultant media, and anaerobic culturing was performed in a nitrogen atmosphere at 37° C. for 72 hours, to thereby yield a composition containing 1,4-dihydroxy-2-naphthoic acid in an amount of 3 µg/ml (50 L). The aforementioned activated culture broth was prepared by inoculating *Propionibacterium freudenreichii* (2% (w/v)) into a TPYG medium (trypticase (BBL) (8 g), phytone peptone (BBL) (3 g), beer yeast extract (5 g), L-cysteine hydrochloride (0.5 g), glucose (20 g), $K_2HPO_4$ (2 g), $KH_2PO_4$ (3 g), $MgCl_2.6H_2O$ (0.5 g), $FeSO_4.7H_2O$ (10 mg), $H_2O$ (1,000 ml), pH 6.5), followed by anaerobic culturing by means of the GasPak method at 37° C. for 72 hours.

Example 2

Production Process for Composition Containing a High Concentration of DHNA

Skim milk powder was dissolved in water such that the skim milk powder concentration became 10 to 20% (w/w), and protease [Amano A] (product of Amano Pharmaceutical Co., Ltd.) was added to the resultant solution such that the amount of the protease was 0.25% (w/w) on the basis of the entirety of the skim milk powder, followed by enzymatic degradation of the resultant mixture at 47° C. for six hours. During the course of enzymatic degradation, the pH of the mixture was maintained at 6.8 by use of an aqueous potassium carbonate solution. The resultant reaction mixture was heated at 85° C. for five minutes to inactivate the enzyme, and then water was added to the resultant mixture such that the skim milk powder concentration became 10% (w/w). After bear yeast extract (product of Asahi Breweries, Ltd.) was added to the resultant mixture such that the amount of the extract was 5% (w/w) on the basis of the entirety of the skim milk powder, the mixture (1.5 Kg) was placed into a fermenter (volume: 2 L), and then sterilized at 121° C. for seven minutes by use of an autoclave. Nitrogen gas was brought into the fermenter such that the gas flowed above the surface of the resultant medium, the medium was stirred at 150 rpm, and the temperature of the medium was regulated to 33° C. After the medium temperature was stabilized at 33° C., a frozen concentrated starter of *Propionibacterium freudenreichii* ET-3 strain (deposited as FERM BP-8115 with International Patent Organism Depositary, National Institute of Advanced Industrial Science and Technology (Central 6, 1-1-1, Higashi, Tsukuba, Ibaraki, Japan (postal code: 305-8566)), on Aug. 9, 2001) (0.05% (w/w)) was inoculated into the medium, and anaerobic culturing was initiated. Lactose (2% (w/w)) and lactose (1.3% (w/w)) were added to the culture broth 72 hours and 96 hours after initiation of this culturing, respectively. This anaerobic culturing was performed in an nitrogen atmosphere at 33° C. for 120 hours while the pH of the culture broth was maintained at 6.45 by use of a 40% (w/w) aqueous potassium carbonate solution, and as a result, DHNA (30 µg/ml) was produced in the culture broth. After the 120-hour culturing, the amount of the alkali consumed in the culture broth (1.5 kg) was found to be 131 g. Sodium ascorbate was added to the resultant culture broth such that the amount of sodium ascorbate was 0.5% (w/w) on the basis of the entirety of the culture broth, and the pH of the resultant mixture was adjusted to 8.0 by use of an aqueous potassium carbonate solution, followed by cooling to 10° C. The resultant culture broth was stored at 10° C. for two weeks, and as a result, the DHNA content of the culture broth was increased to 40 µg/ml. The above-employed frozen concentrated starter was prepared through the following procedure: an activated culture broth of *Propionibacterium freudenreichii* ET-3 strain (prepared through anaerobic culturing of the strain in a medium predominantly containing the aforementioned protease-treated skim milk powder at 33° C. for 48 hours) (2% (w/w)) was inoculated into a medium predominantly containing the protease-treated skim milk powder, followed by culturing at 33° C. for 72 hours; after completion of culturing, the culture broth was collected and then subjected to centrifugation, to thereby increase the bacterium cell concentration by a factor of about 20; and an appropriate amount of the resultant product was placed in a sterilized container, frozen at −80° C. or lower, and then stored at −80° C.

Example 3

Concentration of the Composition Obtained in Example 1 by Means of Column Chromatography A column was filled with Diaion HP-20 (4 L), and the column was washed with a 0.5% (w/v) aqueous sodium ascorbate solution. Thereafter, the composition obtained in Example 1 (40 Kg) was added to the column. Subsequently, a water-soluble fraction was removed from the composition by use of a 0.5% (w/v) aqueous sodium ascorbate solution (8 L). Thereafter, an ethanol eluent (12 L) containing 0.5% (w/v) sodium ascorbate was added to the column, to thereby elute DHNA. The ethanol-eluted fraction was concentrated by use of an evaporator, to thereby produce the composition of the present invention (10 g) containing DHNA (115 mg).

Example 4

Concentration of the Composition Obtained in Example 1 by Use of a Rotary Evaporator Sodium ascorbate (0.5% (w/w)) was added to the composition obtained in Example 1 (5 Kg), and the resultant mixture was concentrated by a factor of five by use of a rotary evaporator, to thereby produce the composition of the present invention (1 Kg) containing DHNA (15 mg).

Since each of the compositions of Examples 1 through 3 is produced by use of a propionic acid bacterium, which is employed for producing cheese, the invention compositions obtained in Examples 1 through 3 can be employed in foods and beverages, without being subjected to any treatment.

Example 5

Purification of DHNA

The concentrate (culture broth) obtained in Example 2 was dissolved in a 0.5% (w/v) aqueous sodium ascorbate solution (1 L) whose pH was adjusted to 4.5, and the resultant solution was subjected to extraction with ethyl acetate (1 L) three times. The thus-obtained ethyl acetate layers were mixed together, and then subjected to dehydration with anhydrous sodium sulfate (200 g), followed by concentration under reduced pressure. After the resultant concentrate was dissolved in methanol (80 mL), and an aliquot (4 mL) of the resultant solution was purified by use of a C18 column. Sodium ascorbate was added to the resultant DHNA elution fraction (retention time: 21 to 31 minutes) such that the sodium ascorbate content was 25% (w/v), and then the resultant mixture was concentrated under reduced pressure. The resultant concentrate (800 mL) was subjected to extraction with ethyl acetate (300 mL) twice, and then subjected to dehydration with anhydrous sodium sulfate (50 g), followed by concentration under reduced pressure. The final purified product was identified as DHNA as a result of structural analysis by means of 500-MHz $^1$H-NMR spectroscopy. Through the above procedure, DHNA (115 mg) was produced from the culture broth (40 L).

Column: Capcell Pak C18 SG120, $\phi$50×500 mm, Lot. 930210 (product of Shiseido Co., Ltd.)
Mobile phase:acetonitrile:methanol:water:acetic acid=20:40:200:0.1 (pH: 7.0 (adjusted with 5% aqueous ammonia))
Temperature: room temperature
Flow rate: 100 mL/min
Injection amount: 4 mL
Detector: UV 254 nm
<NMR data of the final purified product>
$^1$H-NMR (500 MHz, MeOH-d$_4$): δ 8.39 (1H, d, J=8.3 Hz), 8.23 (1H, d, J=8.3 Hz), 7.69 (1H, dd, J=8.3, 6.9 Hz), 7.60 (1H, dd, J=8.3, 6.9 Hz), 7.23 (1H, s)

Example 6

Acute Toxicity Test

The DHNA-containing composition described in Example 2 was subjected to an acute toxicity test by use of five mice (five weeks old: commercially available ICR mice, habituated for seven days). The composition was administered to each of the mice for five consecutive days (maximum daily dose: 78.3 mg/kg (DHNA: 0.9 ($\approx$115×(78.3/(10×1000))) mg/kg)), and the thus-administered mice were observed for 14 days. As a result, none of the mice died, and none of the mice were confirmed to exhibit abnormality in terms of body weight, behavior, and dissected organs.

Example 7

Preparation Method for Food Encorporating the DHNA-Containing Composition of the Present Invention (Tablet Preparation)

The composition obtained in Example 1 (10 Kg) was freeze-dried at a temperature of −50° C. for 24 hours, to thereby yield freeze-dried powder (1 Kg). Subsequently, the powder (40% (w/w)) was incorporated into a tablet base material containing glucose (80% (w/w)), dry corn starch (10% (w/w)), palatinit powder (7% (w/w)), and citric acid (3% (w/w)), and the resultant material was tableted each tablet weighing 0.5 g.

Example 8

Preparation Method for Food Incorporating the DHNA-Containing Composition of the Present Invention (Milk Beverage Preparation 1)

Sodium ascorbate (15 g) and the DHNA-containing composition obtained in Example 2 (125 mg) were added to raw milk (10 Kg), and the resultant mixture was homogenized and then sterilized at 130° C. for two seconds. Every 100 ml of the resultant product was charged into a container.

Example 9

Preparation Method For Food Incorporating the DHNA-Containing Composition of the Present Invention (Milk Beverage Preparation 2)

An activated culture broth of *Propionibacterium freudenreichii* ET-3 strain (FERM P-18454) (60 ml) was inoculated into a medium predominantly containing protease-treated whey powder (the medium was prepared through the following procedure: beer yeast extract (product of Asahi Breweries, Ltd.) (0.1% (w/v)) was added to a solution obtained through two-hour protein degradation (50° C., pH 7.0) of a solution containing 10 wt. % whey powder by use of protease (Amano A, product of Amano Pharmaceutical Co., Ltd.), and the resultant mixture (50 L) was placed in a jar fermenter and then sterilized at 121° C. for seven minutes), followed by anaerobic culturing at 35° C. and a pH of 6.0 for 90 hours, and sodium ascorbate (0.5% (w/v)) was added to the resultant culture broth, to thereby yield the composition of the present invention. The thus-obtained composition (177.5 ml) was added to raw milk (9822.5 ml), and the resultant mixture was homogenized and then sterilized at 130° C. for two seconds. Every 100 ml of the resultant product was charged into a container (DHNA content: 11 μg/100 ml).

The aforementioned activated culture broth was prepared by means of the same process as described in Example 1, except that the incubation temperature was changed to 35° C.

Example 10

Effect of the Invention Composition on Abdominal Ailments Upon Milk Beverage Ingestion 1

The milk beverage prepared in Example 8 was employed as a test beverage, and a milk beverage which had been prepared in a manner similar to that of Example 8 by use of a non-fermented medium was employed as a control beverage. The subjects of the test were selected from among humans who exhibited low β-galactosidase activity in the small intestine when they were subjected to measurement of breath hydrogen concentration upon ingestion of milk, and thus were considered to suffer from lactose intolerance. Specifically, the subjects were 15 humans (seven males and eight females, mean age: 28.07±3.41) who underwent a lactose load test by use of the control beverage (400 ml), and exhibited an increase in breath hydrogen concentration by about 20 ppm or more within six hours after ingestion of the beverage.

The subjects were instructed to abstain from ingesting any food or beverage (except for water) from 22:00 on the day prior to testing to 17:00 on the day of testing. At 10:00 on the day of testing, the control beverage (400 ml) was orally administered to each of the subjects. Until 17:00 of the day, a questionnaire on abdominal conditions was filled out by the subject (every 30 minutes), and the breath was sampled from the subject (every hour). One week later, the test beverage was administered to each of the subjects in a manner similar to the control beverage administration. The subjects were not previously informed of the types of these beverages.

The breath of each of the subjects was sampled by use of a Tedlar bag having a cock (volume: 1 L) (GL Sciences, Inc.), and hydrogen gas analysis was performed by use of a gas chromatograph (GC-8A, Shimadzu Corporation) under the following analysis conditions: column: molecular sieve 5A (3 mm×2 m), oven temperature: 40° C., carrier gas: argon, detector: TCD (thermal conductivity detector).

A questionnaire on abdominal conditions was handed out to each of the subjects, and was filled out by the subject every 30 minutes. Abdominal distention was rated with numerical points in accordance with the following criteria:

4: significant abdominal flatulence as compared with the state immediately after ingestion, 3: moderate abdominal flatulence as compared with the state immediately after ingestion, 2: slight abdominal flatulence as compared with the state immediately after ingestion, and 1: no perceivable change as compared with the state immediately after ingestion. These numerical ratings as obtained at 30-minute intervals (from 30 minutes to six hours) after ingestion were accumulated. Any other abdominal conditions, including diarrhea, abdominal pain, and tympanites (borborygmus), were also described in the questionnaire.

Figure 2:
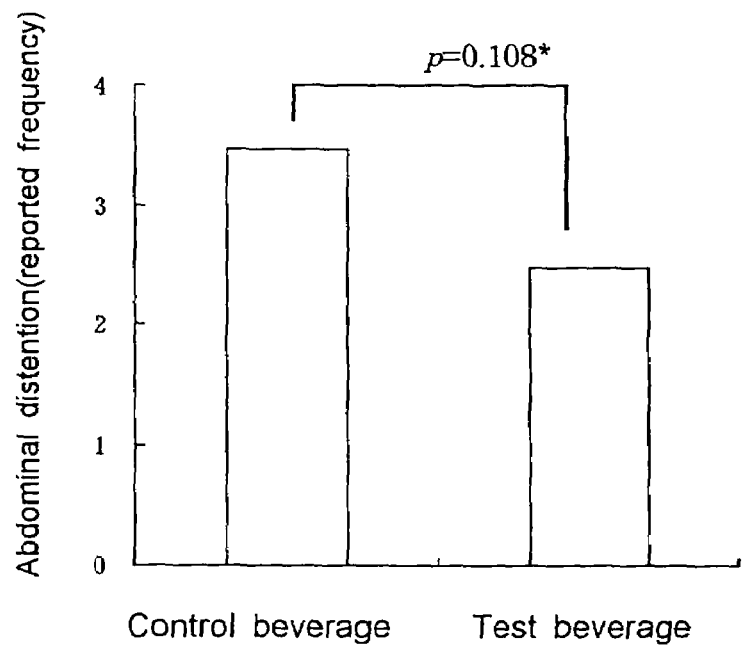
FIG. 2 is a graph showing the frequency of abdominal distention reported by subjects until six hours has elapsed after ingestion of the milk beverage incorporating the composition of the present invention containing a high concentration of DHNA.
Figure 3:
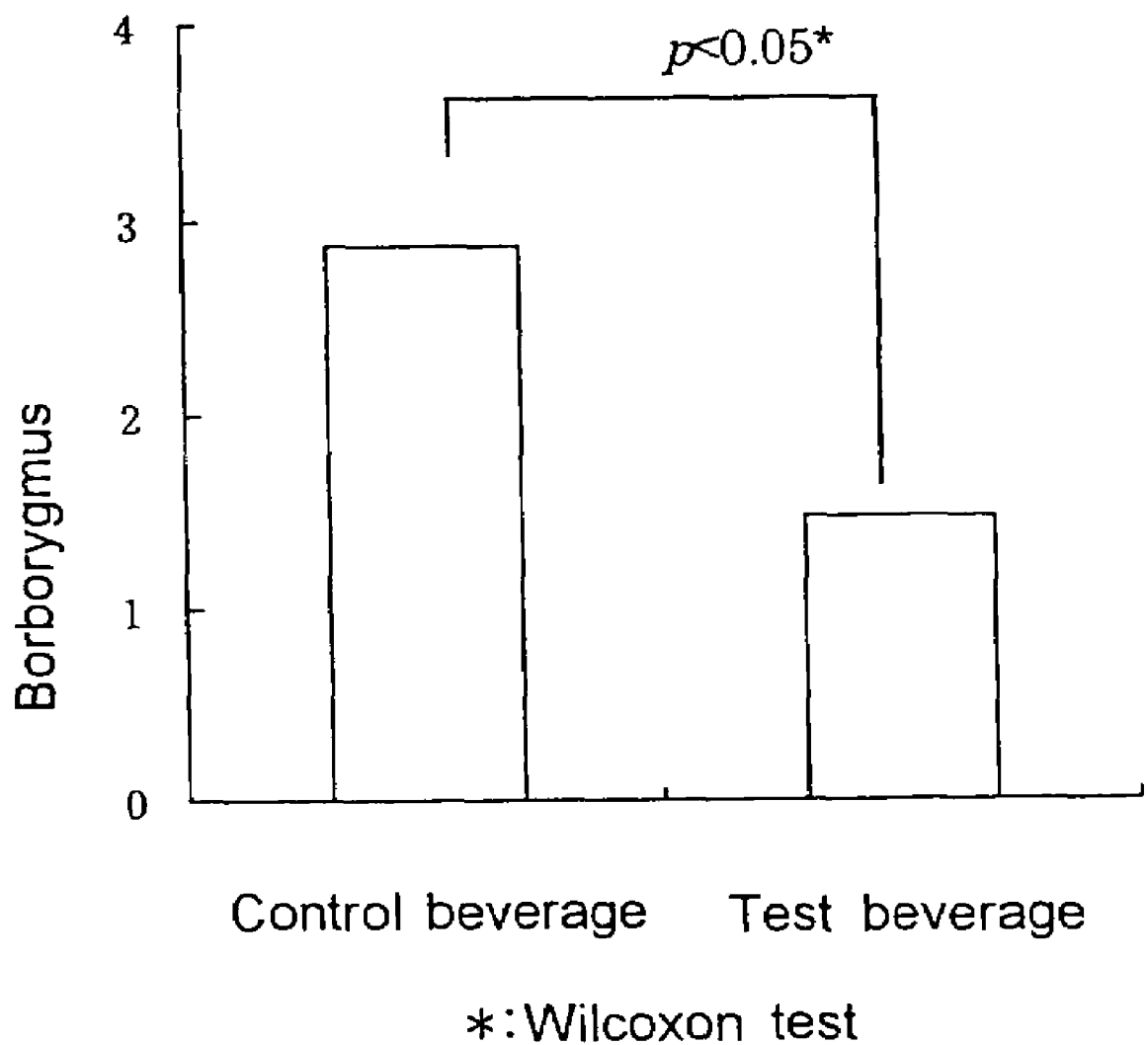
FIG. 3 is a graph showing the frequency of tympanites (borborygmus) reported by subjects until six hours has elapsed after ingestion of the milk beverage incorporating the composition of the present invention containing a high concentration of DHNA.

The evaluation results regarding abdominal conditions from the time immediately after ingestion of the milk beverages to six hours after ingestion thereof are as follows. In the case of ingestion of the control beverage, the cumulative value of the abdominal distention score was found to be 17.93±4.83. In contrast, in the case of ingestion of the test beverage, the cumulative value was found to be 15.93±3.65, which is significantly lower than the value obtained in the case of the control beverage (Wilcoxon test, $p<0.05$) (FIG. 1). In the case of ingestion of the control beverage, the frequency of abdominal distention reported by the subjects until six hours elapsed after ingestion was found to be 3.47±3.11. In contrast, in the case of ingestion of the test beverage, the abdominal distention frequency was found to be 2.47±2.90, which is lower than the abdominal distention frequency obtained in the case of ingestion of the control beverage ($p=0.108$) (FIG. 2). In the case of ingestion of the control beverage, the frequency of tympanites (borborygmus) reported by the subjects until six hours elapsed after ingestion was found to be 2.87±2.75. In contrast, in the case of ingestion of the test beverage, the tympanites frequency was found to be 1.47±2.10, which is significantly lower than the tympanites frequency obtained in the case of ingestion of the control beverage ($p<0.05$) (FIG. 3). Meanwhile, in the case of ingestion of the control beverage, two subjects complained of diarrhea, but, in the case of ingestion of the test beverage, no subjects complained of diarrhea. In the case of ingestion of the control beverage, the number of subjects who did not suffer from abdominal ailments was two, but, in the case of ingestion of the test beverage, the number of such subjects was increased to six (Table 2).

In the case of ingestion of the control beverage, the average value of maximum increases in breath hydrogen concentration was found to be 42.9±13.7 ppm. In contrast, in the case of ingestion of the test beverage, the average value of maximum increases in breath hydrogen concentration was found to be 34.7±17.6 ppm, which is lower than the average value obtained in the case of ingestion of the control beverage (Wilcoxon test, $p=0.051$) (Table 2).

TABLE 2

Effects of ingestion of milk beverage incorporating the DHNA-containing composition on abdominal ailments and breath hydrogen concentration

| Subjects | | | Ingestion of control beverage | | Ingestion of test beverage | |
|---|---|---|---|---|---|---|
| No. | Age | Sex | Breath hydrogen concentration* | Abdominal condiitions[§] | Breath hydrogen concentration* | Abdominal conditions[§] |
| 1 | 27 | Female | 30.2 | B, C | 21.8 | B |
| 2 | 25 | Female | 50.0 | N | 33.9 | N |
| 3 | 28 | Female | 19.2 | B, C | 6.7 | C |
| 4 | 24 | Female | 32.1 | B, C | 13.6 | B |
| 5 | 26 | Male | N.T. | C | N.T. | C |
| 6 | 32 | Male | N.T. | C | N.T. | N |
| 7 | 28 | Male | N.T. | C | N.T. | C |
| 8 | 27 | Female | 54.8 | A, B, C | 46.6 | B, C |
| 9 | 27 | Male | 51.0 | C | 44.2 | N |
| 10 | 32 | Male | 41.2 | N | 21.5 | N |
| 11 | 25 | Female | 42.2 | B | 38.1 | B, C |
| 12 | 23 | Female | 30.8 | B | 59.1 | N |
| 13 | 34 | Female | N.T. | A, C | N.T. | N |
| 14 | 33 | Male | 63.2 | C | 60.0 | C |
| 15 | 30 | Male | 57.7 | C | 35.7 | C |
| Mean ± S.D. | | | 42.9 ± 13.7 | | 34.7 ± 17.6 | |

*Maximum increases in breath hydrogen concentration (ppm)
[§]A: Diarrhea, B: Abdominal pain, C: Tympanites, N: No subjective symptom
N.T.: Not tested.

Example 11

Effect of the Invention Composition on Abdominal Ailments Upon Milk Beverage Ingestion 2

Culturing of *Propionibacterium freudenreichii* IFO 12424 strain was performed in a manner similar to that in Example 9. The thus-obtained culture broth (5 Kg) was concentrated by a factor of five by use of an evaporator, to thereby yield a composition (1 Kg) containing DHNA (45 mg). A milk beverage was prepared from the thus-obtained composition (35.5 g), raw milk (10 kg), and sodium ascorbate (15 g), and the resultant milk beverage was subjected to testing in a manner similar to that in Example 10. In the case of ingestion of the milk beverage containing the composition of the present invention, effects substantially similar to those obtained in Example 10 were obtained, and abdominal ailments upon milk beverage ingestion were found to be alleviated.

Example 12

Effect of DHNA on Promoting Calcification of Osteoblasts

Human osteoblasts (SaM-1), which had been cultured from long bone periosteum of a 20-year-old male obtained during fracture surgery, were employed. The SaM-1 cells exhibited all the characteristic features of osteoblasts (Koshihara, Y. et al.: In Vitro Cell. Dev. Biol., 25: 37-43, 1989). SaM-1 has been known to promote calcification in the presence of 2 mM of α-glycerophosphoric acid in a 1α, 25 (OH)$_2$ D$_3$ concentration-dependent manner (Koshihara, Y. et al.: Biochem. Biophys. Res. commun., 145: 651-657, 1987).

The above-obtained SaM-1 cells of 18 PDL (population doubling level) were inoculated into a 12-well plate, and cultured until the cells reached a confluent state. Subsequently, α-glycerophosphoric acid, which is a calcification promoting agent, was added to the resultant culture broth such that the α-glycerophosphoric acid content became 2 mM. DHNA ($10^{-7}$ M to $10^{-5}$ M) was added to the culture broth, followed by culturing for 32 days. For a control, DMSO (a solvent) was added to the culture broth such that the DMSO content became 0.1%. The media of the test culture broth and the control culture broth were exchanged every second day with a DHNA-containing medium and a DMSO-containing medium, respectively. The degree of calcification was represented by the amount of Ca, which constitutes hydroxyapatite.

The Ca content of extracellular matrix was quantified by use of a kit (Calcium C Test Wako) based on the o-cresolphthalein complexone method (OCPC method) (Gitleman, H. J.: Anal. Biochem., 18: 520-531, 1967).

Figure 4:
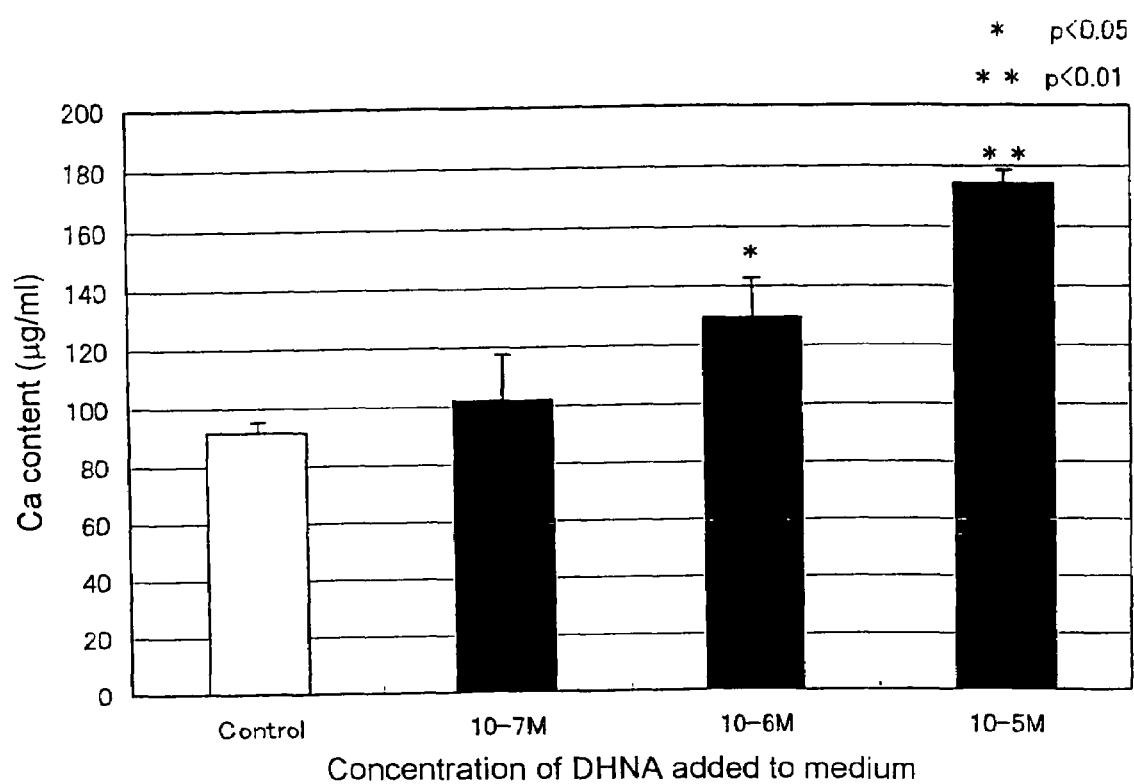
FIG. 4 is a graph showing the effect of DHNA on promoting calcification of osteoblasts.

After completion of culturing, the resultant cells were washed with a Hanks' solution. Cold 5% perchloric acid (0.5 ml/well) was added to the cells, followed by shaking extraction at 4° C. for 15 minutes. The resultant extract (25 μL) was mixed with a buffer (2.5 mL), and subsequently a coloring solution (containing OCPC (0.4 mg/mL) and 8-quinolinol) (250 μL) was added to the resultant mixture and then stirred for five minutes. Thereafter, the resultant reaction mixture was subjected to measurement by use of an absorbance meter (570 nm) (FIG. 4). As shown in FIG. 4, DHNA promotes calcification in a concentration-dependent manner.

Example 13

Effect of DHNA on Animal Model With Osteoporosis Induced by FK-506

Figure 5:
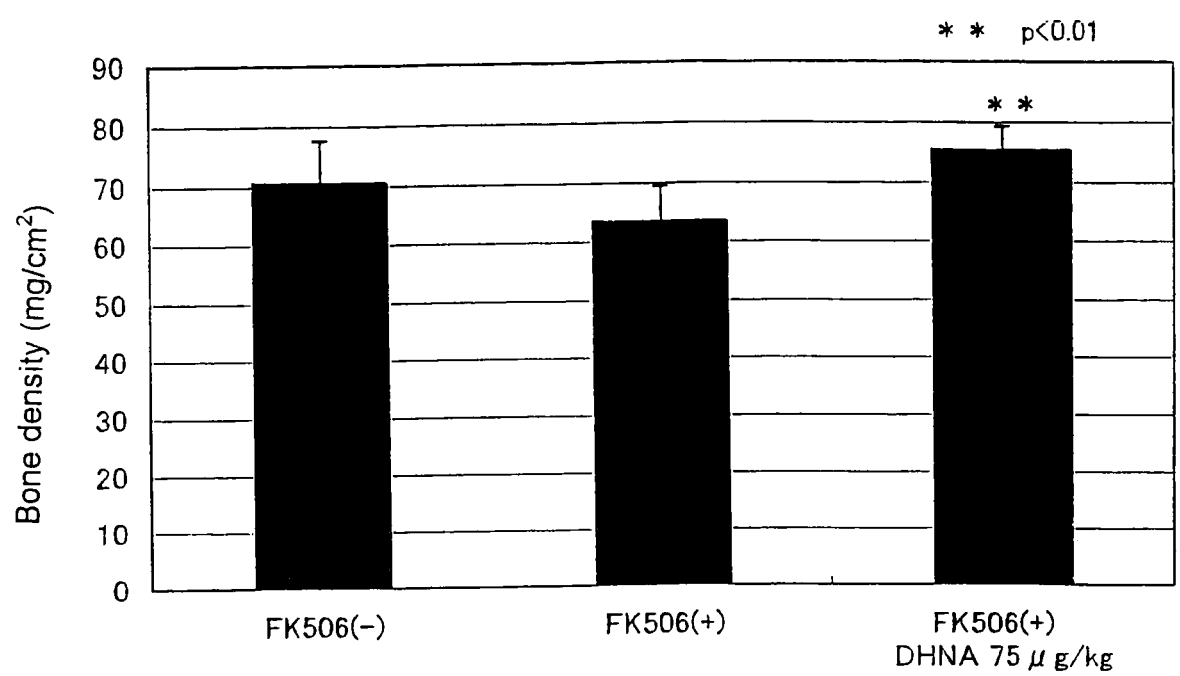
FIG. 5 is a graph showing the effect of DHNA on suppressing a decrease in bone density.

As has been known, administration of FK-506, which is known as an immunosuppressive agent, to an animal induces osteoporosis-like conditions (J. Hard Tissue Biology, 103-107, 10 (2), 2001). As has been suggested, formation of osteoclasts proceeds by means of hyperexpression of RANKL (osteoclast differentiation factor), which is expressed on osteoblasts, and bone resorption exceeds bone formation, resulting in such osteoporosis-like conditions. FK-506 (1 mg/kg) was intraperitoneally administered to ICR male mice (eight weeks old) for 10 consecutive weeks. During the 10-week FK-506 administration, a feed (CRF-1, product of Oriental Yeast Co., Ltd.) was arbitrarily ingested into the mice, and DHNA (75 µg/kg) which had been suspended in a 1% aqueous DMSO (dimethyl sulfoxide) solution was orally administered to each of the mice every day. As a result, the bone density of the mice in the DHNA administration group was found to be significantly higher than that of the mice in the control group (FK 506 (+)), and a decrease in bone density due to FK 506 administration was found to be suppressed by means of DHNA (FIG. 5).

INDUSTRIAL APPLICABILITY

A DHNA-containing composition produced through the industrial production process for DHNA of the present invention is derived from a microorganism, and thus the composition exhibits excellent safety. When orally administered, the composition containing a high concentration of DHNA improves intestinal flora. In addition, the composition can be employed for alleviating abdominal ailments which occur upon ingestion of milk, and for preventing or treating metabolic bone diseases. By virtue of its non toxicity, the composition can be ingested over a long period of time.

The invention claimed is:

1. A method for treating an abdominal ailment comprising administering to a subject in need thereof a composition comprising a culture broth comprising a microorganism of the genus *Propionibacterium* and a therapeutically effective amount of 1,4-dihydroxy-2-naphthoic acid or a salt thereof.

2. The method according to claim 1, wherein the abdominal ailment is one or more abdominal ailments selected from the group consisting of an abdominal ailment caused by lactose intolerance, abdominal distention, tympanites, borborygmus, flatulence, abdominal pain and diarrhea.

3. The method according to claim 1, wherein the therapeutically effective amount of 1,4-dihydroxy-2-naphthoic acid or a salt thereof is from 0.03 µg to 3 µg per kg body weight per day.

4. The method according to claim 1, wherein the therapeutically effective amount of 1,4-dihydroxy-2-naphthoic acid or a salt thereof is from 0.1 µg to 1 µg per kg body weight per day.

5. The method according to claim 1, wherein the composition comprises a pharmacologically or sitologically acceptable salt of 1,4-dihydroxy-2-naphthoic acid.

6. The method according to claim 5, wherein the pharmacologically or sitologically acceptable salt of 1,4-dihydroxy-2-naphthoic acid is selected from the group consisting of an acetate, a benzenesulfonate, a benzoate, a bicarbonate, a lactate and a citrate.

7. The method according to claim 1, wherein the microorganism is selected from the group consisting of *P. freudenreichii, P. thoenii, P. acidipropionici, P. jensenii, P. avidum, P. acnes, P. lyphophilum* and *P. granulosam*.

8. The method according to claim 1, wherein the microorganism is *P. freudenreichii*.

9. The method according to claim 1, wherein the microorganism is selected from the group consisting of *P. freudenreichii* IFO 12424, *P. freudenreichii* ATCC 6207, and *P. freudenreichii* ET-3 FERM BP-8115.

10. The method according to claim 1, wherein the composition further comprises cheese, yoghurt or milk.

11. The method according to claim 1, wherein the composition further comprises an auxiliary agent.

12. The method according to claim 11, wherein the auxiliary agent is selected from the group consisting of an excipient, a binder, a disintegrating agent, a lubricant, a flavoring agent, a deodorant, a dissolution promoter, a suspending agent and a coating agent.

13. The method according to claim 1, wherein the composition is in a form suitable for oral administration.

14. The method according to claim 1, wherein the composition is in a form selected from the group consisting of a food, a beverage, a drug, a tablet, a capsule, a granule, a powder and a syrup.

* * * * *